US011884616B2

United States Patent
Egolf et al.

(10) Patent No.: US 11,884,616 B2
(45) Date of Patent: Jan. 30, 2024

(54) PROCESSES AND APPARATUSES FOR OPERATING A HYDROCARBON CONVERSION ZONE

(71) Applicant: UOP LLC, Des Plaines, IL (US)

(72) Inventors: Bryan J. Egolf, Crystal Lake, IL (US);
Christopher D. DiGiulio, Elmhurst, IL (US); William Yanez, Belvidere, IL (US); Ka L. Lok, Buffalo Grove, IL (US); Elie J. Fayad, Munster, IN (US);
Haibo Yu, Rolling Meadows, IL (US);
Kristen E. Allaire, Chicago, IL (US);
Falaah Falih, Mount Prospect, IL (US);
Jeffrey R. Grott, Chicago, IL (US);
Sujay R. Krishnamurthy, Hoffman Estates, IL (US); Hari S. Bajpai, Gurugram (IN); Phillip F. Daly, Palatine, IL (US); Matthew R. Zuraski, Schaumburg, IL (US); Hosoo Lim, Mount Prospect, IL (US); Joseph Peterson, Otsego, MI (US); Michael R. Van de Cotte, Palatine, IL (US);
Steven A. Bradley, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 17/936,988

(22) Filed: Sep. 30, 2022

(65) Prior Publication Data

US 2023/0212095 A1    Jul. 6, 2023

Related U.S. Application Data

(60) Provisional application No. 63/266,307, filed on Dec. 31, 2021.

(51) Int. Cl.
*C07C 5/333* (2006.01)
*B01J 19/18* (2006.01)

(52) U.S. Cl.
CPC .......... *C07C 5/333* (2013.01); *B01J 19/1862* (2013.01); *B01J 2219/0004* (2013.01);
(Continued)

(58) Field of Classification Search
CPC .. C07C 5/333; C07C 2527/02; B01J 19/1862; B01J 2219/0004; B01J 2219/00058; B01J 2219/00065
See application file for complete search history.

(56) References Cited

U.S. PATENT DOCUMENTS 5,461,016 A * 10/1995 Bradley ............... C10G 35/095
502/66
5,723,707 A   3/1998 Heyse et al.
(Continued)

FOREIGN PATENT DOCUMENTS

CN      1045411 A     9/1990
CN    105585409 A     5/2016
(Continued)

OTHER PUBLICATIONS https://www.lyncis.lt/wp-content/uploads/Online-Analyzer-Iron-and-Steel.pdf.
(Continued)

*Primary Examiner* — Thuan D Dang

(57) ABSTRACT

Processes and apparatus for reforming hydrocarbons to reduce the impact of contaminants created by non-catalyst coking. The reaction zone receives sulfur to inhibit the impact, and a control index is used to control the determine conditions with generally lower pressures. Additionally, a compression zone, pressure control zone and combustion
(Continued)

zone operation are provided for the operation of the reaction zone at the generally lower pressures.

17 Claims, 3 Drawing Sheets

(52) U.S. Cl.
CPC .................. *B01J 2219/00058* (2013.01); *B01J 2219/00065* (2013.01); *C07C 2527/02* (2013.01)

(56) References Cited

U.S. PATENT DOCUMENTS

| | | |
|---|---|---|
| 8,192,691 B2 | 6/2012 | Fecteau et al. |
| 8,323,416 B2 | 12/2012 | Bradley et al. |
| 8,906,223 B2 | 12/2014 | Moser et al. |
| 9,023,298 B2 | 5/2015 | Moser et al. |
| 2013/0158316 A1 | 6/2013 | Moser et al. |
| 2014/0302614 A1 | 10/2014 | Porter et al. |
| 2020/0263922 A1 | 8/2020 | Vu et al. |

FOREIGN PATENT DOCUMENTS

| | | |
|---|---|---|
| EP | 3083900 A1 | 10/2016 |
| WO | 2008076595 A1 | 6/2008 |
| WO | 2015094655 A1 | 6/2015 |

OTHER PUBLICATIONS

Grabke, Hans Jürgen, Carburization, Carbine Formation, Metal Dusting, Coking, UDK 669.1.784:630.179.11, IISSN: 1580-2949, 2002.
Trimm, David L., Fundamental Aspects of the Formation and Gasification of Coke, Pyrolysis: Theory and Industrial Practice, 203-232, Acedemic Press, 1983, ISBN: 0-12-048880-9.
Wei, Q. et al., Microprosses of coke formation in metal dusting, Materials and Corrosion, 50, 628-633 (1999).
Bonnet, F., et al., Filamentous carbon formation caused by catalytic metal particles from iron oxide, Materials and Corrosion 2003, 54, No. 11, pp. 870-880.
Towfighi, Jafar et al., Coke Formation Mechanisms and Coke Inhibiting Methods in Pyrolysis Furnaces, Journal of Chemical Engineering of Japan, vol. 35, No. 10, pp. 923-937, 2002.
International Search Report from corresponding PCT application No. PCT/US2022/082416, dated May 1, 2023.
Written Opinion from corresponding PCT application No. PCT/US2022/082416, dated May 1, 2023.

\* cited by examiner

PROCESSES AND APPARATUSES FOR OPERATING A HYDROCARBON CONVERSION ZONE

RELATED APPLICATIONS

This application claims priority to U.S. Provisional Patent Application Ser. No. 63/266,307, filed on Dec. 31, 2021, the entirety of which is incorporated herein by reference.

FIELD OF THE INVENTION

This invention relates generally processes and apparatuses for operating a hydrocarbon conversion zone, and more particularly to operating such processes to reduce damage to catalyst from non-catalyst coke.

BACKGROUND OF THE INVENTION

The dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers, and other products which are well known to those skilled in the art. A process for the conversion of paraffins to olefins involves passing a paraffin stream over a highly selective catalyst, where the paraffin is dehydrogenated to the corresponding olefin. The dehydrogenation reaction is achieved under operating conditions selected to minimize the loss of feedstock. The typical process involves the use of a reactor (e.g., radial flow, fixed bed, fluidized bed, and the like) where a paraffin feedstock is contacted with a dehydrogenation catalyst under reaction conditions.

Typically, in such a reactor, a hydrocarbon feedstock and a hydrogen-rich gas are preheated and charged to a reforming zone containing typically two to five reactors in series. Each of the reactors also receive a catalyst. The effluent from the first reactor is withdrawn, heated, and passed to the second reactor. The effluent from the second reactor is withdrawn, reheated and passed to the third reactor. The withdrawal and reheating of the effluent continue until the last reactor and is typically referred to as a radial flow. From the last reactor, the effluent is withdrawn and processed further.

Metal-catalyzed coking introduces contaminants which limit the operating window for the reactors, and significantly impacts the available yield and catalyst inventory for operators. Specifically, iron and other metal contaminants can be introduced to the system by coking on various reactor internals and other equipment surfaces, or on contaminants charged to the unit within the feed hydrocarbon stream. The iron and other metals that may be introduced by non-catalyst coking can agglomerate on the catalyst and otherwise permanently reduce the catalyst activity. As described herein, "non-catalyst coking" refers to coke that is not initiated on the catalyst as a byproduct of its chemical reactions. Rather, it is coke that initiates on other surfaces that are exposed to the process streams and catalyst streams, such as the surfaces of conduits, lines, pipes, heat exchangers, reactors, or other pieces of equipment.

It is known to use sulfur as a means to manage the impacts of contaminants in the reactor. However, sulfur decreases activity of the catalyst and thus lowers the yield, of the desired or intended reactions. Accordingly, there remains an ongoing need for an effective and efficient processes for controlling such a reactor and reaction processes.

SUMMARY OF THE INVENTION

It has surprisingly been found that by operating at lower pressures, the impact of the contaminants from the non-catalyst coking may be controlled. Examples such as 2002—Grubke and 2003—Bonnet disclosed metallurgical comparisons observed by decomposition of CO or CH4 to surface carbon and hydrogen. Extending these to higher molecular weight hydrocarbons anticipates a significant pressure and hydrogen dependency. Earlier work by 1983—Albright and 2002—Towfighi disclosed a pathway through surface condensation of heavy aromatics, which can be found in trace levels within naphtha feeds; however, Towfighi cited this pathway as relatively unimportant below 700° C. Further to this, 1999-Wei disclosed the interaction of gas phase inhibitors on both metal surfaces and surface carbon species. Accordingly, in the present invention, operating conditions for the reactor(s) may be based on a sulfur control index. The sulfur control index is a function of various parameters and can be developed for each reactor. Once a particular sulfur control index is developed or determined, one or more operating conditions may be selected as a target or desired condition and other operating conditions may be adjusted based on the sulfur control index and the selected condition. In other words, for example, an operating pressure for a reactor may be selected, and then a temperature of the reactor may be adjusted to a temperature based on the sulfur control index. In addition, the present invention provides additional actions to be undertaken which may also address and reduce the opportunities for non-catalyst coking.

Moreover, as noted above, the present processes, generally, involve lower pressures than conventionally operated units. Accordingly, the present invention also provides various configurations and arrangements that address the use of a reactor with a generally lower pressure. For example, the present processes contemplate adjustments for compressing vapor streams, suitable transfer of catalyst to a higher-pressure regeneration zone, and operation of the regeneration zone.

Therefore, the present invention may be characterized, in at least one aspect, as providing a process for dehydrogenation of a hydrocarbon by passing a feed stream comprising hydrocarbons to a dehydrogenation zone comprising at least one reactor receiving a dehydrogenation catalyst and being operated at dehydrogenation conditions to provide a product stream enriched in dehydrogenated hydrocarbons compared to the feed stream. The dehydrogenation conditions are based on a sulfur control index determined by one or more of: a pressure of the at least one reactor; a temperature associated with the at least one reactor; and a hydrogen to hydrocarbon ratio. A first dehydrogenation condition in the sulfur control index is selected and a second dehydrogenation condition is adjusted to a corresponding second dehydrogenation condition based on the sulfur control index and the selected, first dehydrogenation condition.

The present invention may also be characterized, broadly, as providing a process for dehydrocyclization of a hydrocarbon by passing a feed stream comprising hydrocarbons and at least 0.1 ppm of sulfur to a dehydrocyclization zone comprising at least one reactor receiving a dehydrocyclization catalyst and being operated at dehydrocyclization conditions to provide a product stream enriched in dehydrogenated hydrocarbons compared to the feed stream. The dehydrocyclization conditions are based on a sulfur control index, the sulfur control index comprising: a pressure of the at least one reactor in a range of between 20 to 90 psig; a temperature associated with the at least one reactor in a range of between 500 to 570° C.; and, a hydrogen to hydrocarbon ratio between 0.5 to 3.5. A first dehydrocyclization condition from the sulfur control index is selected and a second dehydrocyclization condition is adjusted to a corresponding second dehydrocyclization condition based on the sulfur control index and the selected, first dehydrocyclization condition.

Generally, the present invention may also be characterized as providing a process for dehydrogenation of a hydrocarbon by: passing a feed stream comprising hydrocarbons and at least 0.1 ppm of sulfur to a dehydrogenation zone comprising at least one reactor receiving a dehydrogenation catalyst and being operated at dehydrogenation conditions to provide a product stream enriched in dehydrogenated hydrocarbons compared to the feed stream; determining a metallurgy of at least one surface exposed to the feed stream; and, based on the determined metallurgy, controlling the dehydrogenation conditions based a sulfur control index. The sulfur control index comprises: a pressure of the at least one reactor in a range of between 20 to 90 psig; a temperature associated with the at least one reactor in a range of between 500 to 570° C.; and, a hydrogen to hydrocarbon ratio between 0.5 to 3.5. A first dehydrogenation condition from the sulfur control index is selected and a second dehydrogenation condition is adjusted to a corresponding second dehydrogenation condition based on the sulfur control index and the selected, first dehydrogenation condition.

Additional aspects, embodiments, and details of the invention, all of which may be combinable in any manner, are set forth in the following detailed description of the invention.

DETAILED DESCRIPTION OF THE DRAWINGS

One or more exemplary embodiments of the present invention will be described below in conjunction with the following drawing figures, in which.

DETAILED DESCRIPTION OF THE INVENTION

As mentioned above, it has been surprisingly discovered that operating a hydrocarbon reaction zone at lower pressures may reduce the impact of the contaminants from the non-catalyst coking. Accordingly, a sulfur control index may be used to determine one or more operating conditions. The sulfur control index may generally be characterized as a function of pressure, sulfur amount, and LHSV for a given coke precursor. As is known, sulfur decreases activity and yield, but is needed to manage contaminants. Accordingly, the sulfur control index will implicate temperature staging from the perspective of sulfur and contaminant loadings. Generally, the processes can be run at lower pressure and higher LHSV while maintaining sulfur levels at the same level as operations at higher pressure and lower LHSV without decreasing yield. Acceptable levels of sulfur concentration were achieved when operating the process at a pressure in the range of 10-50 psig average across the reaction stages.

With these general principles in mind, one or more embodiments of the present invention will be described with the understanding that the following description is not intended to be limiting.

Figure 1:
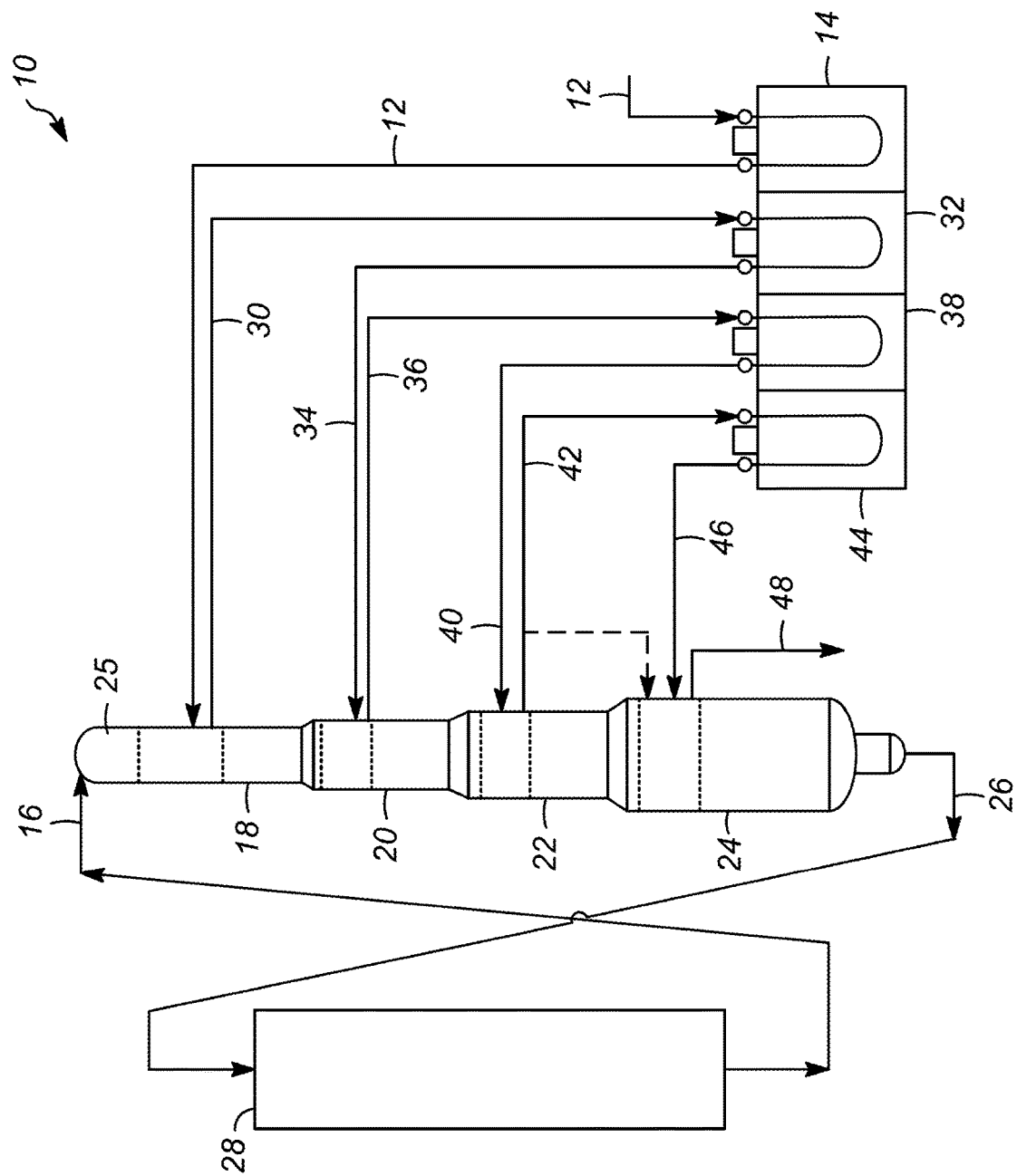
FIG. 1 is a schematic view of a reaction zone used in accordance with one or more embodiments of the present invention.

With reference to FIG. 1, the present invention is directed to a reaction zone 10 for converting hydrocarbons in a hydrocarbon feed stream 12. The hydrocarbon feed stream 12 typically comprises naphthenes and paraffins boiling within the gasoline range. The preferred feed streams 12 includes straight-run naphthas, thermally or catalytically cracked naphthas, partially reformed naphthas, raffinates from aromatics extraction and the like. Usually, such feed streams 12 have been hydrotreated to remove contaminants, especially sulfur and nitrogen. A gasoline-range feed streams 12 may be a full-range naphtha having an initial boiling point from about 40° to about 70° C. and an end boiling point within the range from about 160° to about 220° C., or may be a selected fraction thereof. The feed stream 12 may be heated in a charge heater 14 and passed to the reaction zone 10 along with catalyst particles in a catalyst transfer line 16.

The catalyst used in the present invention are preferably for a dehydrogenation reaction, and in particular for a dehydrocyclization reaction. Catalyst particles for such reactions often include a metallic hydrogenation-dehydrogenation component on a porous inorganic oxide support providing acid sites for cracking and isomerization, is usually employed in catalytic reforming. Most reforming catalyst particles are in the form of spheres or cylinders having an average particle diameter or average cross-sectional diameter from about 1.59 to about 4.76 mm (1/16 inch to about 3/16 inch). Catalyst composites comprising platinum on highly purified alumina or on zeolitic supports are particularly well known in the art. Metallic modifiers that improve product yields or catalyst life, such as rhenium, iridium, tin, and germanium, also may be incorporated into the catalyst.

As shown in FIG. 1, the reaction zone 10 contains a series of four reforming reactors 18, 20, 22, 24 arranged vertically to form a stacked reactor 25. This is merely one configuration and is not intended to be limiting, other configurations may be utilized for practicing the present invention.

Catalyst particles enter the top of the stacked reactor 25 through the catalyst transfer line 16 and pass through the series reforming reactors 18, 20, 22, 24 under gravity flow. After passing through all of the reforming reactors 18, 20, 22, 24, the catalyst particles are withdrawn from the bottom of the stacked reactor 25 by one or more catalyst withdrawal lines 26. Catalyst withdrawn through the catalyst withdrawal lines 26 may be regenerated by the oxidation and removal of coke deposits in a regeneration zone 28. After regeneration, catalyst particles may be again returned to the process and the reaction zone 10 in the catalyst transfer line 16. In addition to including regenerated catalyst, the catalyst in the catalyst transfer line 16 may be partially pre-stabilized with sulfur.

As shown in FIG. 1, the feed stream 12 is heated in charge heater 14 and then passed to the first reforming reactor 18. A first reactor effluent 30 is passed to a first heater 32 to generate a heated second reactor feed 34. A second reactor effluent 36 is passed to another heater 38 to generate a heated third reactor feed 40. A third reactor effluent 42 is passed to another heater 44 to generate a fourth reactor feed 46. A fourth reactor effluent 48 comprises a product stream which can be recovered from the reactor 10 and processed further as is known. In the fixed bed and continuous catalyst regeneration reforming processes, the heaters 14, 32, 38, 44 are commonly used to heat up the feed streams 12, 34, 40, 46 to an elevated temperature.

Operating conditions used for the present process usually include a pressure selected within the range from about 5 to 100 psig, or 20 to 90 psig, or 20 to 40 psig. Reforming conditions include a temperature in the range from about 500 to about 570° C., or 540 to 570° C. The temperatures of each reforming reactors 18, 20, 22, 24 may refer to an inlet temperature of that reforming reactors 18, 20, 22, 24. Additionally, the reforming reactors 18, 20, 22, 24 may be operated such that they have different operating conditions. For example, a catalyst bed in the first reforming reactor 18 may be operated at a temperature that is at least 30° C. lower than a temperature of the other reforming reactors 20, 22, 24.

The reforming conditions in the present invention also typically include providing sufficient hydrogen to provide a hydrogen to hydrocarbon ratio between 0.5 to 3.5, or between 1.2 to 2.2. The liquid hourly space velocity (LHSV) used in the present invention may be is selected from the range from about 0.1 to about 10 $hr^{-1}$, or from about 1 to about 5 $hr^{-1}$.

Various surfaces in the reforming reactors 18, 20, 22, 24 and the heaters 14, 32, 38, 44, for example, may form coke that can damage the catalyst. Accordingly, sulfur is injected, in the form of DMDS (dimethyl disulfide), into the feed stream(s) 12, 34, 40, 46 to counteract the damage to the catalyst from the coke. See, e.g., U.S. Pat. Pub. No. 2013/0158316.

In the various embodiments of the present invention, the operation conditions for the individual reforming reactors 18, 20, 22, 24 are selected and controlled based on a sulfur control index. The sulfur control index is a relationship of operating conditions and parameters that is a function of multiple factors including, for example, sulfur amounts, metallurgy, pressure, temperature, and hydrogen to hydrocarbon ratio. If one or more of the conditions are known or desired, the operating conditions or parameters may be selected so that the reactor conditions fall on the sulfur control index.

In order to determine if the at least one reactor is being operated according to the sulfur control index, a gas-phase sensor may monitor one or more conditions in the reforming reactors 18, 20, 22, 24. For example, a sensor may be used which is configured to detect a specific metal which may be associated with the metallurgy of the equipment used. In a stainless-steel system, iron may be used as a specific metal. In a low-chrome system, alternative metallurgies or carburized samples can be utilized. Examples of sensors are discussed in U.S. Pat. Pub. No. 2014/0302614. It is also contemplated that a microreactor enclosure is provided in which the hydrocarbon feed is analyzed and monitored by thermogravimetric analysis at a defined temperature for the specific metal.

Additionally, a particulate collection system and a sensor may be utilized to determine if the reforming reactors 18, 20, 22, 24 are being operated within stable dehydrogenation conditions. For example, a filtration unit having a filter or other separator may be used to remove particulates from vapor/gas streams. The present invention contemplates analyzing and monitoring the collected particulates for their metallic compositions. Particulates can be broken fines, but high carbon and metals within the fines is an indicator of non-catalyst coking. This analysis can be accomplished by methods including XRD and laser elemental analysis. With the information from the particulate collection system about metal(s) present (or absent), the conditions may be adjusted to reduce the amount of non-catalyst coking occurring. For example, if a high amount of iron is detected, it may be desired to reduce a temperature in one or more of the reforming reactors 18, 20, 22, 24. Accordingly, the sulfur control index may be used to select the other conditions to maintain the operation of the reforming reactors 18, 20, 22, 24 on the sulfur control index.

As discussed, in the present processes, sulfur is used to counteract the impact of non-catalyst coke on the catalyst. To further address or minimize the impact of the non-catalyst coke and other contaminants on the catalyst, it is contemplated that one or more surfaces that the various feed streams 12, 34, 40, 46 are exposed to, for example in the various lines containing these streams 12, 34, 40, 46, are surfaces that are metallurgical coke retardant, or oxidant scale resistant, or both. One exemplary surface is one which has a protective, adherent and coherent chromium oxide film at surface provided by a minimum chromium content of stainless steel to be >10.5%, with preferred combination of coking and corrosion resistance occurs in austenitic stainless steels provided by a combination 8% nickel and 17% chromium. Other metallurgically-bonded coatings are contemplated such as an inorganic refractory oxide or a material selected from ceramics, metal oxides, metal sulfides, glasses, silicas, and other high temperature resistant non-metallic materials. See, U.S. Pat. Pub. No. 2012/0277500. The surfaces may also be improved in-situ by adding compounds to change the ability to reduce the amount of coking, for example by injecting a sulfur compound, such as hydrogen sulfide ($H_2S$), into one or more of the various feed streams 12, 34, 40, 46.

It is further contemplated that the feed streams 12, 34, 40, 46 are treated or otherwise processed before it is passed into the reforming reactors 18, 20, 22, 24. For example, the feed streams 12, 34, 40, 46 may be treated to reduce a size, a quantity, or both of metallurgical coke precursors in the feed streams 12, 34, 40, 46. Thus, the feed streams 12, 34, 40, 46 may be filtered to remove iron-based precursors to reduce a size, a quantity, or both of metallurgical coke precursors in the feed streams 12, 34, 40, 46.

As discussed above, compared with conventional operation conditions, the present processes use lower pressure in conjunction with sulfur injection. However, using lower pressure may require modifications and changes to equipment because of the relationship of the reforming reactors 18, 20, 22, 24 to other equipment used in the reforming zone 10 and the regeneration zone 28.

Figure 2:
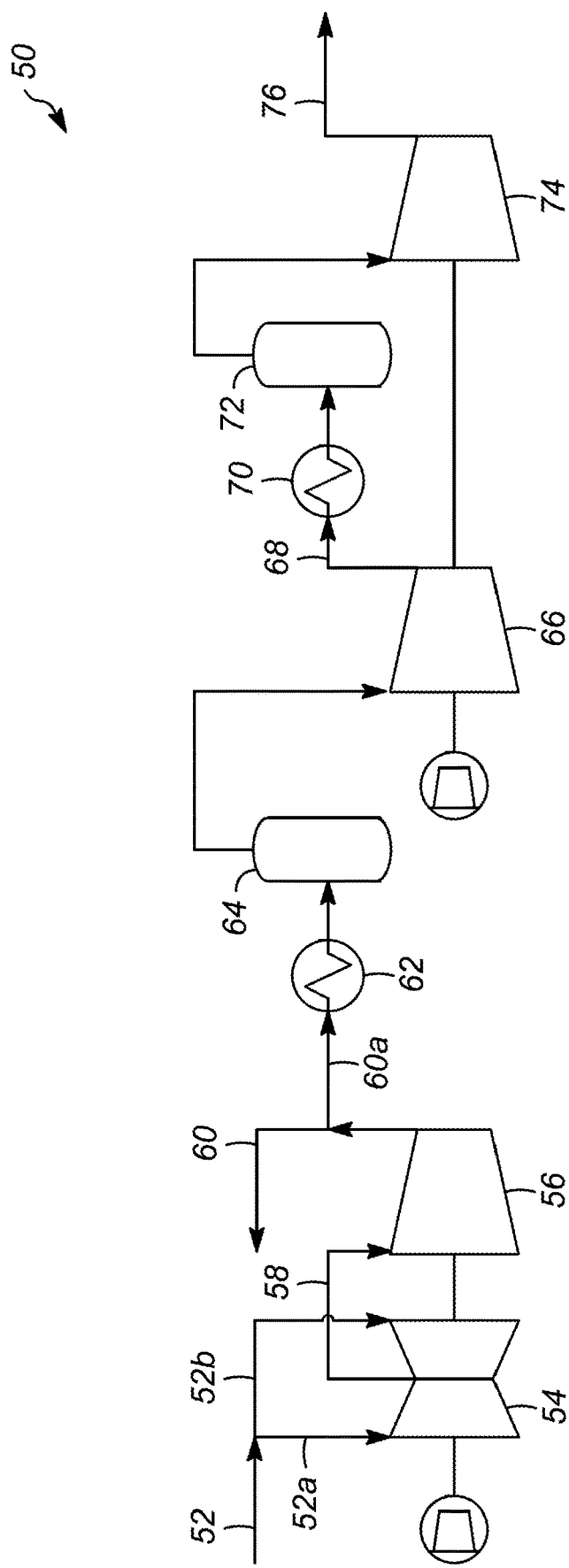
FIG. 2 is a schematic view of a compression zone used in accordance with one or more embodiments of the present invention; and, FIG. 3 is a schematic view of a regeneration zone and pressure control zone used in accordance with one or more embodiments of the present invention.

For example, the present invention addresses the impact of the lower pressure on a recycle gas stream. Specifically, with a lower pressure, it may be difficult for a compressor on the recycle gas stream to adequately achieve a high enough pressure output. Accordingly, the reforming reactors 18, 20, 22, 24 of FIG. 1 may receive a recycle gas stream that may be generated by separating it from the fourth reactor effluent 48. As shown in FIG. 2, the reaction zone 10 may therefore include a compression zone 50 that receives a gas stream 52 from one or more of the reforming reactors 18, 20, 22, 24 (in FIG. 1). The compression zone 50 is a 2-stage compression zone having a first compressor 54 and a second compressor 56. The gas stream 52 is split into two low pressure streams 52a, 52b. The first compressor 54 is configured to receive each of the low-pressure streams 52a, 52b and provide a single high-pressure stream 58 (relative to the pressure of the low-pressure streams 52a, 52b). The high-pressure stream 58 is passed to the second compressor 56 which increases the pressure thereof to provide the recycle gas stream 60. This compression zone 50 allows the for the effective and efficient compression of a gas stream from the reforming reactors 18, 20, 22, 24 when using the lower pressures contemplated herein. Additionally, stream 58 is a recycle gas stream which may be used for catalyst transfer, purging, and heat exchange.

As also shown in FIG. 2, if needed, a portion 60a of the recycle gas stream 60 may be cooled in a heat exchanger 62 and passed to a drum 64 and then to a compressor 66. An output 68 of the compressor 66 may be cooled in a second heat exchanger 70, then passed to a second drum 72 and then compressed in another compressor 74. An output 76 of this compressor 74 is a compressed hydrogen stream that may be processed further by hydrotreating or passed to a pressure swing adsorption unit for additional purification.

It is also contemplated to address the disparity of operating pressures in the regeneration zone 28 compared with the reaction zone 10. More specifically, while the reforming reactors 18, 20, 22, 24 of the reaction zone 10 may be operated with generally lower pressure ranges, the regeneration zone 28 may be operated with a higher pressure range. Accordingly, the present invention contemplates solutions to transferring catalyst between the two zones 10, 28.

Figure 3:
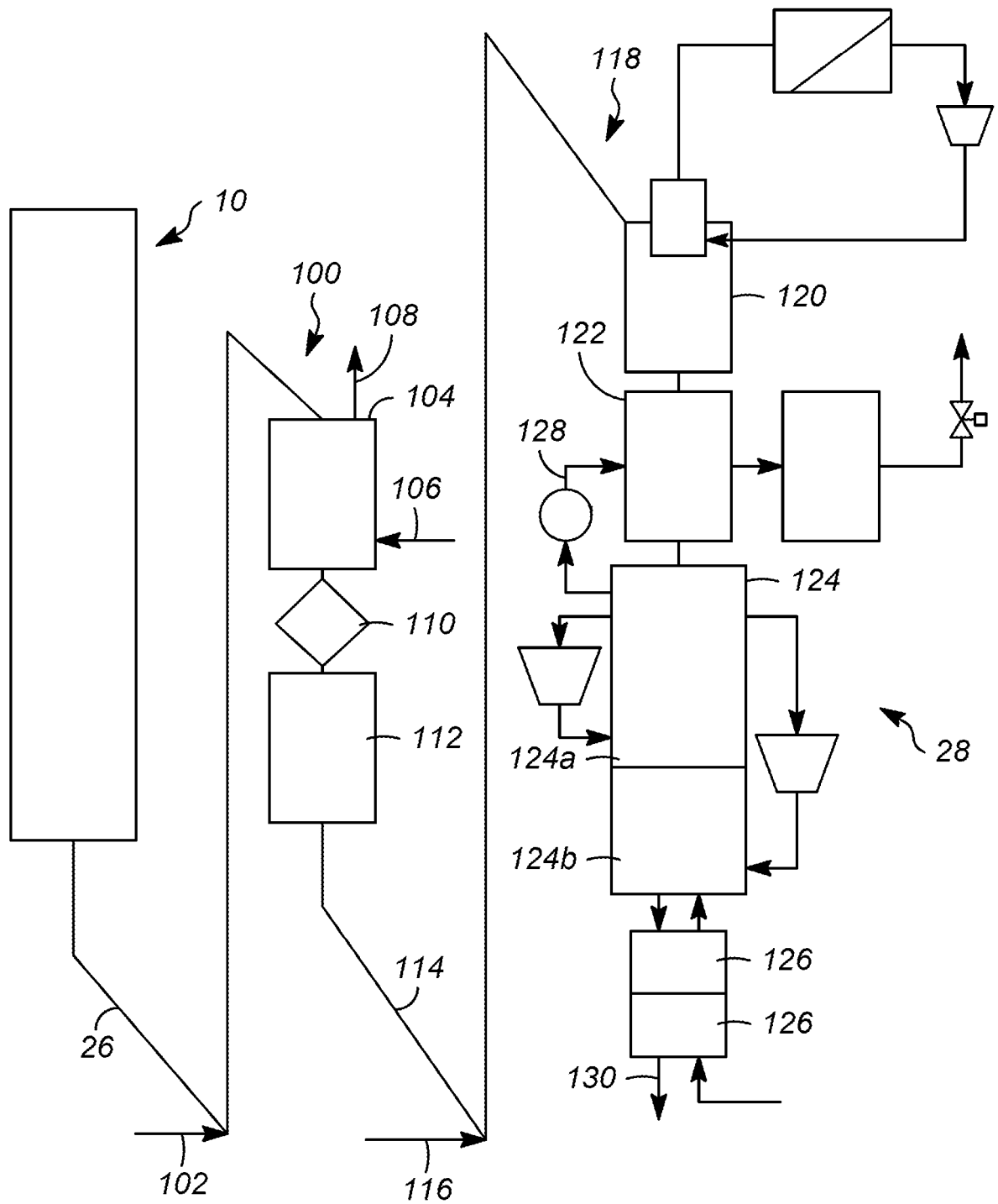

For example, turning to FIG. 3, if the reaction zone 10 is operated at approximately 15 psig and the regeneration zone 28 is operated at 45 psig, a pressure control system 100 may be provided between the two zones.

Accordingly, as shown in FIG. 3, a lift gas 102 may be used to transfer particles in the catalyst transfer line 26 to a first surge vessel 104. The first surge vessel 104 may also receive a purge gas stream 106 which may be one of reactor products streams 30, 36, 42, 48 (FIG. 1). In the first surge vessel 104, the catalyst particles and hydrocarbons separate. A vent gas 108 from the first surge vessel 104 may be combined with the effluent 48 from the last reactor 24. The catalyst particles will fall to the bottom of the first surge vessel 104.

Disposed below the first surge vessel 104 is a lock hopper 110. As is known the lock hopper 110 includes entrance and exit valves that open sequentially. When the entrance valve is open catalyst from the first surge vessel 104. The entrance valve may then be closed. Once closed, the exit valve may be opened and the catalyst in the lock hopper 110 will fall into a second surge vessel 112 disposed vertically below the lock hopper 110. After the exit valve is closed, the process may repeat itself. From the second surge vessel 112, a stream of catalyst 114 can be transported to a regenerator 118 of the regeneration zone 28 with a lift gas 116, such as an inert gas like nitrogen, at a pressure that is greater than the operating pressures in the reaction zone 10.

The regenerator 118 includes various zones for removing coke form the catalyst, replacing active additives like halogens, and otherwise conditioning the spent catalyst be returned to the reaction zone 10 as regenerated catalyst. For example, the regenerator may include a disengaging zone 120, an adsorption zone 122, a combustion zone 124, and treatment zones 126.

In the disengaging zone 120 the catalyst particles are separated from the lift gas. In the adsorption zone 122, the catalyst particles contact with a vent gas 128 from the combustion zone 124 and adsorb active additives that are in the vent gas 128. From the adsorption zone 122, the particles pass into the combustion zone 124 which is operated at a temperature and pressure to remove coke from the catalyst.

From the combustion zone 124, the particles may pass through the various treatment zones 126 that may add additional active additives, dry, and cool the catalyst, before it may be passed back to the reaction zone 10 in a catalyst transfer line 130. As will be appreciated, a lock hopper or other device may be used due to the pressure differential between the regeneration zone 28 and the reaction zone 10.

Returning to the combustion zone 124, it is contemplated that the combustion zone 124 include two combustion zones 124a, 124b, each having its own operating temperature. Catalyst particles are first passed to the first combustion zone 124a, and then to the second combustion zone 124b. According to the present invention, it is contemplated that a temperature of the first combustion zone 124a is lower than a temperature of the second combustion zone 124b. Additionally, the temperature of the first combustion zone 124a is based on a condition of catalyst in the second combustion zone 124b. Accordingly, if an amount of catalyst in the second combustion zone 124b has coke that exceeds a desired or threshold amount, the temperature in the first combustion zone 124a may be increased. This operation scheme attempts to avoid using higher temperatures in the combustion zone 124 and therefore reduce damage to the catalyst which may be caused by the higher temperatures.

In general, the present invention provides for effective and efficient operation of a reaction zone with lower pressures but the same or similar throughput while addressing the impact of non-catalyst coke on the catalyst by using the sulfur control index.

EXAMPLES

A series of equipment surface fouling experiments were conducted across a temperature range of 400 to 720° C., hydrocarbon residence times from 0.1 to 1.1 seconds, $H_2S/H_2$ ratios from 0.3 to 1.6 ppmv, and hydrocarbon partial pressures from 2 to 20 psig. The feed to the equipment surface sample comprised mixtures of hydrocarbon and hydrogen with a ratio of hydrogen to hydrocarbon from 2 to 6 mol/mol.

The weight of equipment surface sample was directly measured during the test, as well as measured in some cases through ex-situ weight analysis. TABLE 1, below, provides a few illustrative examples of these experiments.

TABLE 1

| | Feed Properties | | | | Operating Conditions | | | | | |
|---|---|---|---|---|---|---|---|---|---|---|
| | N + A (% w) | IBP (° F.) | EP (° F.) | Metallurgy | $H_2S/H_2$ (mol/mol) | Residence (sec) | P_HC (psig) | Temp (° C.) | d(W/A)/dt (mg/m2/min) | INDEX |
| Feed1 | 69.3 | 117 | 388 | 1.25% Cr | 0.5 | 0.1 | 2.4 | 631 | 0.00005 | 339 |
| | | | | 1.25% Cr | 0.3 | 0.1 | 2.4 | 621 | 0.00009 | 1119 |
| | | | | 18% Cr | 0.3 | 0.1 | 2.4 | 681 | 0.00003 | 539 |

TABLE 1-continued

| | Feed Properties | | | | Operating Conditions | | | | | |
|---|---|---|---|---|---|---|---|---|---|---|
| | N + A (% w) | IBP (° F.) | EP (° F.) | Metallurgy | H2S/H2 (mol/mol) | Residence (sec) | P_HC (psig) | Temp (° C.) | d(W/A)/dt (mg/m2/min) | INDEX |
| Feed 2 | 37.2 | 182 | 350 | 1.25% Cr | 0.3 | 0.5 | 15.9 | 681 | 0.00005 | 816 |
| | | | | 1.25% Cr | 0.3 | 1.1 | 15.9 | 681 | 0.00012 | 903 |
| | | | | Oxidized 1.25% Cr | 0.3 | 0.5 | 10.6 | 641 | 0.00008 | 279 |

As the results in TABLE 1 show, a given feed and surface type experiences fouling as a strong function of temperature, residence time, sulfur content, and hydrocarbon partial pressure. Thus, a sulfur index can be created using these effects.

Equation 1 summarizes the sulfur index created using the experiments described above.

[EQ. 1]

$$\text{INDEX} = Const(\text{Feed}) \cdot Const(\text{Metallurgy}) \cdot e^{\frac{-137.6 \frac{kcal}{mol}}{R_{IG} Temp}} \cdot \left[ \frac{(\text{HC\_Residence})^{2.03}}{P_{HC}^{1.14} \cdot \left(\frac{P_{H2S}}{P_{H2}}\right)^{4.00}} \right]$$

First, the experiments were sorted into groups of constant residence time, sulfur content, and hydrocarbon partial pressure. Next the ln(weight gain) versus 1/T was plotted for each group. Next, the slopes and intercepts of each of these unique linear relationships were plotted as a function of dependent variables residence time, sulfur content, and hydrocarbon partial pressure. These sets of linear relationships were then combined to yield the sulfur index shown in Equation 1. The solution of the index for the example data is also provided within TABLE 1, above.

TABLE 2, below, illustrates how to make use of this sulfur index for an operating unit.

TABLE 2

| H2HC | Pressure | P7-Conversion @1.3-1.7 LHSV | RON-kBBL |
|---|---|---|---|
| 1.0-2.2 | 25-50 | 49-56 | 2423-2193 |
| 2.2-4.8 | 50-100 | 56-69 | 2193-1907 |
| 4.8-7.0 | 100-150 | 69-72 | 1907-1790 |

For the purposes of this example, it is assumed that an operating unit is running at a pressure from 50 to 100 psig and a ratio of hydrogen to hydrocarbon of 2.2 to 4.8 mol/mol. It may be desirable to improve octane-barrel yields by reducing pressure, but also preserve the same operating margin as the base case against the fouling of equipment internals. Accordingly, the sulfur control index may be used.

First, EQ. 1 is used to calculate the sulfur index for the base case. Next, EQ. 1 is used again at a lower 25-50 psig, but this time the sulfur index and pressure are known and the hydrogen to hydrocarbon must be solved to achieve the same sulfur index as in the base case. The result is a hydrogen to hydrocarbon of 1.0-2.2 mol/mol.

TABLE 3, below, illustrates how to make use of this sulfur index for a unit considering equipment additions and/or changes.

TABLE 3

| | H2HC (mol/mol) | Pressure (psig) | H2S/H2 (ppm mol/mol) | P7-Conversion @1.2-1.8 LHSV |
|---|---|---|---|---|
| Fe-Oxidizes | 1-5 | 25-100 | 0.5-2.0 | 23-76% |
| <17% Chrome Steels | 1-5 | 25-100 | 0.5-2.0 | 29-90% |
| >17% Chrome Steels | 1-5 | 25-100 | 0.5-2.0 | 70-99+% |

For the purposes of this example, it is assumed that an operating unit is running at a pressure from 25-100 psig and a hydrogen to hydrocarbon ratio of 1-5 mol/mol. It may be desirable to improve conversion by adding a reaction stage that extends their paraffin conversion rating through new equipment, but also to preserve the same operating margin as the base case against the fouling of equipment internals. Once again, the sulfur control index may be used.

First, EQ. 1 is used to calculate the sulfur index for the base case. Next, EQ. 1 is used again, but this time the sulfur index and conversion target are known and the metallurgy selection must be solved to achieve the same sulfur index as in the base case. The result is that section absent of iron oxide ingress and guarded with steels having >15% chrome can sustain 23-47% higher conversion.

As shown be appreciated, the specific EQ. 1 is based on the parameters of the data and assumptions in TABLE 1. Each system is different and the results of similar experiments may provide different equations that may be used as the sulfur control index. However, with the sulfur control index, a targeted efficient and effective operation of the system may be accomplished.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

SPECIFIC EMBODIMENTS

While the following is described in conjunction with specific embodiments, it will be understood that this description is intended to illustrate and not limit the scope of the preceding description and the appended claims.

A first embodiment of the invention is a process for dehydrogenation of a hydrocarbon, the process comprising passing a feed stream comprising hydrocarbons to a dehydrogenation zone comprising at least one reactor receiving a dehydrogenation catalyst and being operated at dehydrogenation conditions to provide a product stream enriched in dehydrogenated hydrocarbons compared to the feed stream, wherein the dehydrogenation conditions are based on a sulfur control index determined by one or more of a pressure of the at least one reactor; a temperature associated with the at least one reactor; and a hydrogen to hydrocarbon ratio; wherein a first dehydrogenation condition in the sulfur control index is selected and a second dehydrogenation condition is adjusted to a corresponding second dehydrogenation condition based on the sulfur control index and the selected, first dehydrogenation condition. An embodiment of the invention is one, any or all of prior embodiments in this paragraph up through the first embodiment in this paragraph, wherein the feed stream comprises at least 0.5 ppm of sulfur. An embodiment of the invention is one, any or all of prior embodiments in this paragraph up through the first embodiment in this paragraph, wherein the at least one reactor comprises a plurality of reforming reactors, each reforming reactor comprising an inlet, and wherein the temperature associated with the at least one reactor comprises an inlet temperature at each reforming reactor. An embodiment of the invention is one, any or all of prior embodiments in this paragraph up through the first embodiment in this paragraph, wherein each reforming reactor is operated independently under dehydrogenation conditions based on the sulfur control index. An embodiment of the invention is one, any or all of prior embodiments in this paragraph up through the first embodiment in this paragraph, wherein the hydrogen to hydrocarbon ratio is between 0.5 to 3.5. An embodiment of the invention is one, any or all of prior embodiments in this paragraph up through the first embodiment in this paragraph, wherein the hydrogen to hydrocarbon ratio is between 1.2 to 2.2. An embodiment of the invention is one, any or all of prior embodiments in this paragraph up through the first embodiment in this paragraph, wherein the temperature associated with the at least one reactor is a range of between 500 to 570° C. An embodiment of the invention is one, any or all of prior embodiments in this paragraph up through the first embodiment in this paragraph, wherein the pressure associated with the at least one reactor is a range of between 5 to 100 psig. An embodiment of the invention is one, any or all of prior embodiments in this paragraph up through the first embodiment in this paragraph, wherein the at least one reactor comprises a reforming reactor, and wherein the reforming reactor further receives a recycle gas stream, and wherein the recycle gas stream is compressed in a compression zone having a 2-stage compression with a first stage comprising a compressor that receives two low pressure streams and provides a single high pressure stream with an increased pressure compared to the two low pressure streams. An embodiment of the invention is one, any or all of prior embodiments in this paragraph up through the first embodiment in this paragraph, wherein the catalyst is provided from a regeneration zone being operated at a pressure and temperature to reduce a coking on the catalyst, wherein the pressure of the regeneration zone is greater than the pressure of the at least one reactor, and wherein a pressure control system is provided between the regeneration zone and the at least one reaction zone, the pressure control system comprising a first surge vessel configured to receive a first stream comprising a mixture of spent catalyst from the at least one reactor and a lift gas and a second stream comprising a purge stream; a lock hopper disposed vertically below the first surge vessel; and, a second surge vessel disposed vertically below the lock hopper and configured to provide a high-pressure stream of spent catalyst that is passed to the regeneration zone. An embodiment of the invention is one, any or all of prior embodiments in this paragraph up through the first embodiment in this paragraph, wherein the catalyst is provided from a regeneration zone being operated at a pressure and temperature to reduce a coking on the catalyst, wherein the regeneration zone comprises a first combustion zone a second combustion zone, wherein the catalyst moves from the first combustion zone to the second combustion zone, wherein a temperature of the first combustion zone is lower than a temperature of the second combustion zone, and wherein the temperature of the first combustion zone is based on a condition of the catalyst in the second combustion zone. An embodiment of the invention is one, any or all of prior embodiments in this paragraph up through the first embodiment in this paragraph, wherein a line for providing the feed stream to the at least on reactor comprises a surface that is metallurgical coke retardant, or oxidant scale resistant, or both. An embodiment of the invention is one, any or all of prior embodiments in this paragraph up through the first embodiment in this paragraph, wherein the at least one reactor comprises a plurality of reforming reactors, and wherein a catalyst bed in a first reforming reactor is operated at a temperature that is at least 30° C. lower than a temperature of each other reactor from the plurality of reforming reactors. An embodiment of the invention is one, any or all of prior embodiments in this paragraph up through the first embodiment in this paragraph further comprising reducing a size, a quantity, or both of metallurgical coke precursors in the feed stream before it is passed into the at least one reactor. An embodiment of the invention is one, any or all of prior embodiments in this paragraph up through the first embodiment in this paragraph, wherein reducing a size, a quantity or both of metallurgical coke precursors in the feed stream comprises filtering the feed stream to remove iron-based precursors from the feed. An embodiment of the invention is one, any or all of prior embodiments in this paragraph up through the first embodiment in this paragraph, wherein a gas-phase sensor monitors a condition of the dehydrogenation conditions to determine if the at least one reactor is being operated according to the sulfur control index. An embodiment of the invention is one, any or all of prior embodiments in this paragraph up through the first embodiment in this paragraph, wherein a particulate collection system and a sensor are utilized to determine if the at least one reactor is being operated within dehydrogenation conditions based on the non-catalyst coke control index. An embodiment of the invention is one, any or all of prior embodiments in this paragraph up through the first embodiment in this paragraph, wherein the catalyst comprises regenerated catalyst that has been partially pre-stabilized with sulfur.

A second embodiment of the invention is a process for dehydrocyclization of a hydrocarbon, the process comprising passing a feed stream comprising hydrocarbons and at least 0.1 ppm of sulfur to a dehydrocyclization zone comprising at least one reactor receiving a dehydrocyclization catalyst and being operated at dehydrocyclization conditions to provide a product stream enriched in dehydrogenated hydrocarbons compared to the feed stream, wherein the dehydrocyclization conditions are based a sulfur control index, the sulfur control index comprising a pressure of the at least one reactor in a range of between 20 to 90 psig; a temperature associated with the at least one reactor in a range of between 500 to 570° C.; and, a hydrogen to hydrocarbon ratio is between 0.5 to 3.5; wherein a first dehydrocyclization condition from the sulfur control index is selected and a second dehydrocyclization condition is adjusted to a corresponding second dehydrocyclization condition based on the sulfur control index and the selected, first dehydrocyclization condition. An embodiment of the invention is one, any or all of prior embodiments in this paragraph up through the second embodiment in this paragraph, wherein the hydrogen to hydrocarbon ratio is between 1.2 to 2.2, or the pressure of the at least one reactor is in a range of between 20 to 40, or the temperature associated with the at least one reactor in a range of between 540 to 570° C., or a combination thereof.

A third embodiment of the invention is a process for dehydrogenation of a hydrocarbon, the process comprising passing a feed stream comprising hydrocarbons and at least 0.1 ppm of sulfur to a dehydrogenation zone comprising at least one reactor receiving a dehydrogenation catalyst and being operated at dehydrogenation conditions to provide a product stream enriched in dehydrogenated hydrocarbons compared to the feed stream, determining a metallurgy of at least one surface exposed to the feed stream, and, based on the determined metallurgy, controlling the dehydrogenation conditions based a sulfur control index, the sulfur control index comprising a pressure of the at least one reactor in a range of between 20 to 90 psig; a temperature associated with the at least one reactor in a range of between 500 to 570° C.; and, a hydrogen to hydrocarbon ratio is between 0.5 to 3.5; wherein a first dehydrogenation condition from the sulfur control index is selected and a second dehydrogenation condition is adjusted to a corresponding second dehydrogenation condition based on the sulfur control index and the selected, first dehydrogenation condition.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for dehydrogenation of a hydrocarbon, the process comprising:
   passing a sulfur containing feed stream comprising hydrocarbons to a dehydrogenation zone comprising at least one reactor receiving a dehydrogenation catalyst and being operated at dehydrogenation conditions to provide a product stream enriched in dehydrogenated hydrocarbons compared to the feed stream,
   wherein the dehydrogenation conditions are based on a sulfur control index determined by one or more of: a pressure of the at least one reactor; a temperature associated with the at least one reactor; and a hydrogen to hydrocarbon ratio,
   wherein a first dehydrogenation condition in the sulfur control index is selected and a second dehydrogenation condition is adjusted to a corresponding second dehydrogenation condition based on the sulfur control index and the selected, first dehydrogenation condition, and
   wherein sulfur control index is determined using Equation 1, wherein Equation 1 comprises $$\text{INDEX} = Const(\text{Feed}) \cdot Const(\text{Metallurgy}) \cdot e^{\frac{-137.6 \frac{kcal}{mol}}{R_{IG} \cdot Temp}} \cdot \left[ \frac{(\text{HC\_Residence})^{2.03}}{P_{HC}^{1.14} \cdot \left(\frac{P_{H2S}}{P_{H2}}\right)^{4.00}} \right].$$

2. The process of claim 1, wherein the feed stream comprises at least 0.5 ppm of sulfur.

3. The process of claim 1, wherein the at least one reactor comprises a plurality of reforming reactors, each reforming reactor comprising an inlet, and wherein the temperature associated with the at least one reactor comprises an inlet temperature at each reforming reactor.

4. The process of claim 3, wherein each reforming reactor is operated independently under dehydrogenation conditions based on the sulfur control index.

5. The process of claim 1, wherein the hydrogen to hydrocarbon ratio is between 0.5 to 3.5.

6. The process of claim 1, wherein the temperature associated with the at least one reactor is a range of between 500 to 570° C.

7. The process of claim 1, wherein the pressure associated with the at least one reactor is a range of between 5 to 100 psig.

8. The process of claim 1, wherein the at least reactor comprises a reforming reactor, and wherein the reforming reactor further receives a recycle gas stream, and
wherein the recycle gas stream is compressed in a compression zone having a 2-stage compression with a first stage comprising a compressor that receives two low pressure streams and provides a single high pressure stream with an increased pressure compared to the two low pressure streams.

9. The process of claim 1, wherein the catalyst is provided from a regeneration zone being operated at a pressure and temperature to reduce a coking on the catalyst,
wherein the pressure of the regeneration zone is greater than the pressure of the at least one reactor, and
wherein a pressure control system is provided between the regeneration zone and the at least one reactor, the pressure control system comprising:
a first surge vessel configured to receive a first stream comprising a mixture of spent catalyst from the at least one reactor and a lift gas and a second stream comprising a purge stream;
a lock hopper disposed vertically below the first surge vessel; and,
a second surge vessel disposed vertically below the lock hopper and configured to provide a high-pressure stream of spent catalyst that is passed to the regeneration zone.

10. The process of claim 1, wherein the catalyst is provided from a regeneration zone being operated at a pressure and temperature to reduce a coking on the catalyst,
wherein the regeneration zone comprises a first combustion zone a second combustion zone, wherein the catalyst moves from the first combustion zone to the second combustion zone, wherein a temperature of the first combustion zone is lower than a temperature of the second combustion zone, and wherein the temperature of the first combustion zone is based on a condition of the catalyst in the second combustion zone.

11. The process of claim 1, wherein a line for providing the feed stream to the at least on reactor comprises a surface that is metallurgical coke retardant, or oxidant scale resistant, or both.

12. The process of claim 1, wherein the at least one reactor comprises a plurality of reforming reactors, and wherein a catalyst bed in a first reforming reactor is operated at a temperature that is at least 30° C. lower than a temperature of each other reactor from the plurality of reforming reactors.

13. The process of claim 1 further comprising:
reducing a size, a quantity, or both of metallurgical coke precursors in the feed stream before it is passed into the at least one reactor.

14. The process of claim 13, wherein reducing a size, a quantity or both of metallurgical coke precursors in the feed stream comprises filtering the feed stream to remove iron-based precursors from the feed.

15. The process of claim 1, wherein a gas-phase sensor monitors a condition of the dehydrogenation conditions to determine if the at least one reactor is being operated according to the sulfur control index.

16. The process of claim 1, wherein a particulate collection system and a sensor are utilized to determine if the at least one reactor is being operated within dehydrogenation conditions based on the sulfur control index.

17. The process of claim 1, wherein the catalyst comprises regenerated catalyst that has been partially pre-stabilized with sulfur.

* * * * *